Oct. 25, 1932. W. SIM Plant Pat. 37
CARNATION
Filed July 29, 1932
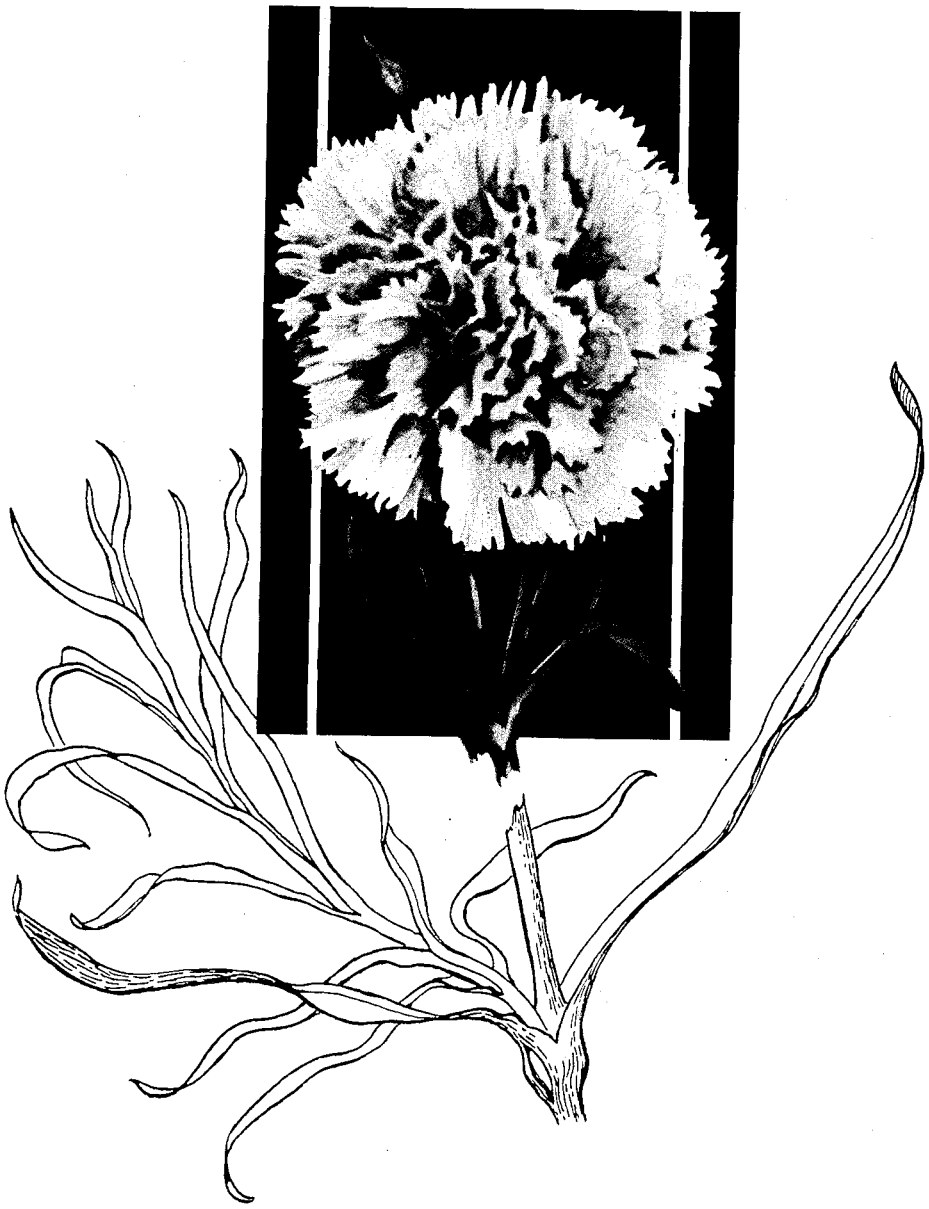
William Sim
by O. M. Kile
PLANT PATENT AGENT Patented Oct. 25, 1932

Plant Pat. 37

UNITED STATES PATENT OFFICE

WILLIAM SIM, OF SAUGUS, MASSACHUSETTS

CARNATION

Application filed July 29, 1932. Serial No. 626,002.

This invention relates to improvements in carnations of the type ordinarily known as perpetual blooming or greenhouse forcing carnations. The object of this invention is to provide a new and improved carnation of the type above mentioned, having blossoms of a distinctive and pleasing color, full and more perfect in form, with a delicate fragrance, and longer lasting qualities, in addition to possessing superior habits of growth and facilitating reproduction by the abundance of its side shoots.

This result I accomplish by crossing two unnamed seedlings in the usual way. The first specimen of this new variety was produced in 1926. For several years thereafter I reproduced this new variety asexually, observed and tested it to make certain that its characters were fixed.

The accompanying illustration shows, in the original, my carnation in approximately its natural size and coloring. The stem shows the characteristic tendency to send out a large number of side shoots suitable for propagation purposes.

The following is a detailed description of my new carnation:

*Habits of growth.*—Vigorous with long, straight, stiff stems and an unusually large number of side shoots each of which if allowed to grow would produce a flower, or which may be used for propagation purposes.

Each plant ordinarily produces twenty to twenty-five flowers per season. While the foliage is long and abundant it cannot be called "grassy" in growth. Notably disease resistant.

*Flowers.*—Very full and almost perfect in formation, having no open centers or irregular formations of any kind; 3 to 3½ inches in diameter when fully opened, very compact and has (in November) 55 to 56 large petals and 6 to 8 small or rudimentary petals; edges of the petals are deeply and somewhat irregularly serrated, some of the petals particularly in the outer course being so deeply cut at the edges as to appear to be side shoots from the main petal. Delicately fragrant.

The prevailing or dominant color effect in nontechnical terms would be called an intense or bright pink. The outer edges of the outer petals are a "deep rose pink" as shown in Plate XII of Ridgeway's Color Standards and Nomenclature, edition of 1912. All the visible portions of the flower viewed from the top, with the exception of the tips of the outer whorl of petals, are "rose color" as shown in Plate XII of Ridgeway's Color Standards and Nomenclature. The color tones become deeper toward the center of the flower. The under side of each petal is somewhat lighter than its upper surface and each petal is white at its base. This white is, however, not visible except upon spreading the petals apart. An occasional petal has a narrow white streak running from its outer edge part way down toward its base. This white streak is not noticeable, however, except on close examination.

The seed pod is large, four celled, and mounted by four white pistils which are concealed by the petals and remain almost straight until the flower withers. No pollen has been found on the many specimens examined. The flowers of this variety have the ability to remain fresh-looking and full-colored for extremely long periods after being cut and placed in water—ten days to two weeks at room temperatures and three weeks at a lower temperature.

*Calyx.*—The calyx is tough and strong and has six sections or lips. These lips are cut down approximately one-third the length of the entire calyx cup, thus allowing expansion room for the opening flower and avoiding bursting. This freedom from bursting is an important feature in a carnation having such full petalage. The calyx cup is gracefully tapering rather than blunt and bulky. Four main bracts and two leafy bracts are found at the base of the calyx.

*Buds.*—Short and rounded when immature.

*Stems and foliage.*—Stiff stems hold the flowers erect even though stems are very long; of forest green color overcast with a light bloom. The leaves are somewhat longer and wider than in most other varieties and do not curl. The tendency to throw out side shoots is strongly developed. This not only accounts for its prolific production of flowers but for the ease and rapidity with which the variety can be propagated. On a typical stem there will be 4 to 6 side shoots each capable of developing a flower, or of propagating a new plant if removed and properly handled. The vigorous growing habits of this variety make it unnecessary to remove the flower from the central stalk when a good growth of side shoots for propagation purposes is desired. Each plant will produce both flowers and numerous side shoots at the same time.

The more important features which in combination quickly distinguish my new carnation from all other known varieties are:

First, its distinctive shades of intense, deep pink, combined with deeply serrated petals.

Second, the firm, full petalage of the flower and almost perfect formation, with full high center.

Third, the gracefully tapering, strong, non-bursting calyx cup with six lips.

Fourth, its vigorous habits of growth with an unusual number of strong side shoots providing prolific blooming and rapid reproduction.

Fifth, its extraordinary lasting qualities.

Sixth, the delicacy of its fragrance.

I claim:

The variety of carnation herein shown and described, characterized particularly by the intense deep pink color of its blossoms, their full and almost perfect formation, delicate fragrance and extraordinary keeping qualities; and by the vigorous growing habits of the plant and its ease of reproduction due to the unusual growth of side shoots.

In witness whereof I affix my signature.

WILLIAM SIM.